United States Patent [19]

Cianci

[11] 4,386,930
[45] Jun. 7, 1983

[54] COLLECTION DEVICE FOR BODY FLUIDS WITH ANTISEPTIC PUMP

[75] Inventor: James P. Cianci, Cary, Ill.

[73] Assignee: The Kendall Company, Boston, Mass.

[21] Appl. No.: 277,499

[22] Filed: Jun. 26, 1981

Related U.S. Application Data

[62] Division of Ser. No. 149,787, May 14, 1980.

[51] Int. Cl.³ .............................................. A61M 5/32
[52] U.S. Cl. .................................... 604/317; 128/760; 128/767
[58] Field of Search ................. 206/219, 221; 220/94; 128/272.1, 272.3, 276, 277, 278, 283, 297, 760, 762, 765, 766, 767, 768, 771, 295, 273, DIG. 24, DIG. 28, 769; 222/130, 212, 215; 141/364, 365, 366; 4/317, 318, 319; 422/37, 28; 604/317, 327

[56] References Cited

U.S. PATENT DOCUMENTS

| | | | |
|---|---|---|---|
| 3,538,518 | 11/1970 | Heike et al. | 4/317 |
| 3,690,320 | 9/1972 | Riely | 128/283 |
| 3,818,910 | 6/1974 | Harris | 128/DIG. 24 |
| 3,870,076 | 3/1975 | Graznak | 137/571 |
| 3,901,235 | 8/1975 | Patel | 128/DIG. 24 |
| 4,159,550 | 7/1979 | Tobin | 4/319 |
| 4,203,443 | 5/1980 | Genese | 128/272.3 |
| 4,229,408 | 10/1980 | Bennett et al. | 422/37 |
| 4,239,622 | 12/1980 | Ridgway | 422/37 |
| 4,241,733 | 12/1980 | Langston et al. | 128/275 |
| 4,259,952 | 4/1981 | Avoy | 128/214 D |
| 4,265,243 | 5/1981 | Taylor | 128/275 |

FOREIGN PATENT DOCUMENTS 109528 6/1968 Denmark ...................... 128/214 G Primary Examiner—Richard J. Apley
Assistant Examiner—J. L. Kruter
Attorney, Agent, or Firm—Powell L. Sprunger

[57] ABSTRACT

A device for collecting body fluids from a patient comprising, a container having a chamber to receive the body fluids. The device has a receptacle associated with the container and having a cavity to retain an antiseptic agent, with the receptacle cavity communicating with the container chamber through a relatively small opening, and a device for generating pressure in the receptacle cavity to cause passage of the agent from the receptacle cavity to the container chamber through the opening.

5 Claims, 4 Drawing Figures

U.S. Patent  Jun. 7, 1983  4,386,930
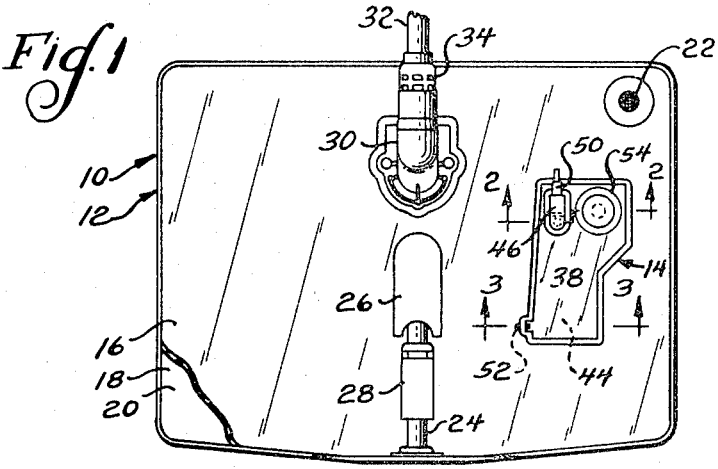
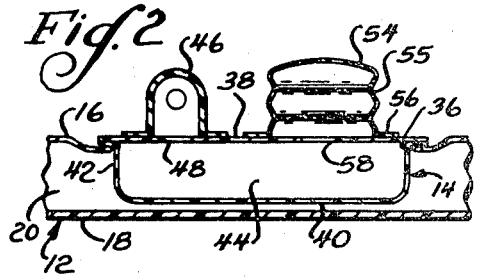 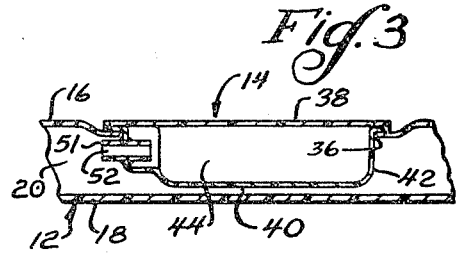
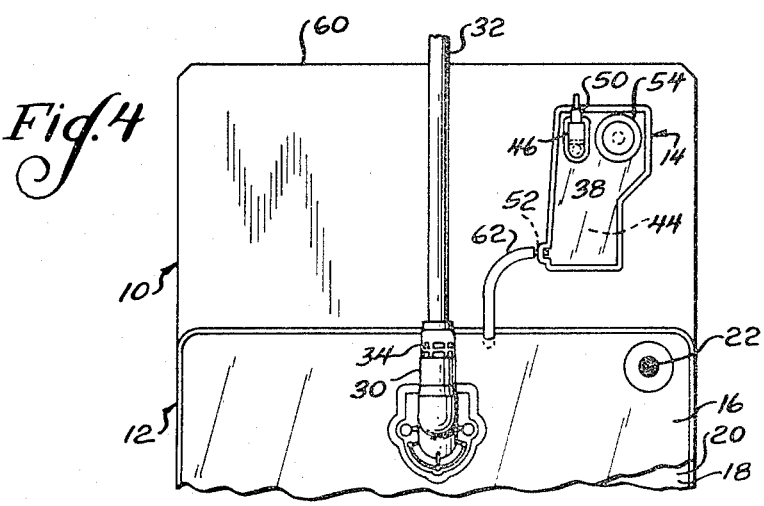

COLLECTION DEVICE FOR BODY FLUIDS WITH ANTISEPTIC PUMP

This is a division, of application Ser. No. 149,787 filed May 14, 1980, now pending.

BACKGROUND OF THE INVENTION

The present invention relates to devices for collecting body fluids from a patient.

Before the present invention, a number of collection bags have been proposed to receive urine from a patient. A catheter is placed in the patient such that it communicates with the patient's bladder, and during catheterization urine drains from the bladder through the catheter and a drainage tube to the collection bag for retention therein. Such systems should be closed to the atmosphere to minimize the possibility of contamination. Nonetheless, a persistent problem has been found in that the collected urine in the bag may become contaminated, resulting in possible undesired retrograde bacteria movement through the system to the bladder of the patient.

SUMMARY OF THE INVENTION

A principal feature of the present invention is the provision of an improved device for collecting body fluids from a patient.

The device comprises, a container having a chamber to receive the body fluids. The device has a relatively rigid receptacle associated with the container and having a cavity to retain an antiseptic agent, means defining a relatively small opening communicating with a lower portion of the receptacle cavity and with the container chamber, valve means communicating with an upper portion of the receptacle cavity, and a flexible bellows attached to a wall of the receptacle and communicating with the cavity.

A feature of the present invention is that the antiseptic agent may be placed in the receptacle cavity through the valve means.

Another feature of the invention is that the bellows may be pressed to generate pressure in the receptacle cavity.

Yet another feature of the invention is that the generated pressure causes flow of the antiseptic agent from the receptacle cavity to the container chamber for mixture with collected body fluids.

Still another feature of the invention is that the antiseptic agent introduced into the collected body fluids minimizes the possibility of bacterial growth in the body fluids.

Further features will become more fully apparent in the following description of the embodiments of this invention and from the appended claims.

DESCRIPTION OF THE DRAWINGS

In the drawings:

FIG. 1 is a fragmentary front plan view of a collection device of the present invention;

FIG. 2 is a fragmentary sectional view taken substantially as indicated along the line 2—2 of FIG. 1;

FIG. 3 is a fragmentary sectional view taken substantially as indicated along the line 3—3 of FIG. 1; and FIG. 4 is a fragmentary front plan view of another embodiment of the collection device of the present invention.

DESCRIPTION OF THE PREFERRED EMBODIMENTS

Referring now to FIGS. 1-3, there is shown a device generally designated 10 for collecting body fluids comprising a container 12 and a receptacle 14. The container 12 has a front wall 16 and a back wall 18 of suitable flexible plastic material joined together at the edges of the front and back walls 16 and 18 to define a chamber 20 in the container 12. The container 12 may have a vent 22 with a bacteria filter of known type to filter bacteria passing from the atmosphere into the container chamber 20. The container 12 may have a tubular section 24 attached to a lower portion of the container front wall 16 and communicating with the chamber 20, with an outer end of the tubular section 24 being received in a pocket 26 on the front wall 16 in a storage position of the tubular section 24. The tubular section 24 may have a suitable clamp 28 which prevents passage of urine through the tubular section 24 when the clamp 28 is closed. When it is desired to drain urine from the container chamber 20, the outer end of the tubular section 24 is removed from the pocket 26 and the clamp 28 is opened in order to permit passage of urine through the tubular section 24, after which the clamp 28 is closed and the tubular section 24 is again inserted into the pocket 26 in the storage position of the tubular section 24.

The container 12 may have a hollow connector 30 in the form of a drip chamber attached to the front wall 16 of the container 12 and communicating with the container chamber 20. As shown, the upper portion of the connector 30 is attached to the downstream end of a drainage tube 32, such that the drainage tube 32 communicates with the connector 30. If desired, the connector 30 may have a vent 34 with a bacteria filter of known type to filter bacteria from air passing from the atmosphere into the connector 30 through the vent 34. In use, a catheter (not shown) is passed through the urethra of a patient until the catheter communicates with the patient's bladder, and a proximal end of the catheter extending outside the patient is attached to the upstream end of the drainage tube 32. During catheterization, urine drains through the catheter, drainage tube 32, and the connector 30 into the container chamber 20 for collection therein. Although the described system is closed to the atmosphere, it has been found that bacteria may form in the collected urine in the chamber 20.

The front wall 16 of the container 12 has an enlarged opening 36, and the receptacle 14 is received in the opening 36 with a portion of the receptacle 14 located in the container chamber 20. As shown, the receptacle 14 is attached to the container front wall 16 peripherally around the opening 36 by suitable means, such as by adhesive. The receptacle 14 has a front wall 38 generally aligned with the front wall 16 of the container 12, a back wall 40 located in the container chamber 20, and a side wall 42 connecting the front and back walls 38 and 40 and extending peripherally around the receptacle 14, such that the front wall 38, the back wall 40, and the side wall 42 define a cavity 44 in the receptacle 14. In a preferred form, the walls of the receptacle 14 are made from a relatively rigid plastic material.

The receptacle 14 has a hollow connector 46 attached to the front wall 38, such that the connector 46 communicates with the cavity 44 through an aperture 48 in the front wall 38. Also, the receptacle has a valve assembly 50 attached to an upper portion of the connector 46.

The valve assembly 50 is of known type and actuates to the open position responsive to contact of the valve assembly 50 by the tip of a syringe.

The receptacle 14 has a tubular portion 51 defining a relatively small opening 52 communicating between the receptacle cavity 44 and the container chamber 20. The receptacle opening 52 is located adjacent a lower portion of the cavity 44, and is sufficiently small, such as 0.030 inches in diameter, such that the surface tension of liquid contained in the cavity 44 will not normally permit the liquid to drain from the cavity 44 to the chamber 20. The receptacle 14 also has a bellows 54 of flexible plastic material, such as polyvinylchloride, having a corrugated wall 55 and a lower edge 56 attached to an upper portion of the receptacle front wall 38, with the inside of the bellows 54 communicating with an upper portion of the cavity 44 through an aperture 58 in the front wall 38. When the bellows 54 is pressed, the depressed bellows 54 generates pressure in the receptacle cavity 44.

In use of the device 10, the tip of a syringe (not shown) is attached to the valve assembly 50 in order to actuate the valve assembly 50 and open the valve assembly 50 to permit a liquid antiseptic agent, such as povidone iodine, to be pumped by the syringe through the valve means 50 and the connector 46 into the receptacle cavity 44. The antiseptic agent will normally remain in the receptacle cavity 44 due to the surface tension of the agent and the relatively small size of the opening 52. However, at periodic intervals during catheterization, the bellows 54 may be pressed in order to generate pressure in the cavity 44, and cause passage of the antiseptic agent from the receptacle cavity 44 into the container chamber 20 through the opening 52. In turn, the antiseptic agent introduced into the collected urine minimizes the possibility of bacterial growth in the urine. In this manner, the collection device of the present invention minimizes the possibility of contamination to the patient's bladder which may be caused by retrograde bacterial movement from the collected urine through the drainage tube 12 to the patient.

Another embodiment of the present invention is illustrated in FIG. 4, in which like reference numerals designate like parts. In this embodiment, the device 10 has a container 12 with walls 16 and 18 defining a chamber 20, and a receptacle 14 with cavity 44, connector 46, valve assembly 50, bellows 54, and small opening 52, as previously described. However, in this embodiment, the container 12 has a header 60 of relatively rigid plastic material located above the container chamber 20. As shown, the receptacle 14 is attached to the header 60, and the device 10 has a tubular section 62 which communicates between the opening 52 of the receptacle 14 and an upper portion of the container chamber 20. The device operates as previously described in connection with the device of FIGS. 1-3. An antiseptic agent may be introduced through the valve means 50 into the receptacle cavity 44, and the bellows 54 may be pressed to generate pressure in the cavity 44 and cause passage of the antiseptic agent through the opening 52 and tubular section 62 into the container chamber 20 where it minimizes the possibility of bacterial growth in the collected urine.

The foregoing detailed description is given for clearness of understanding only, and no unnecessary limitations should be understood therefrom, as modifications will be obvious to those skilled in the art. For example, a liquid deodorizing agent may be placed in the receptacle cavity 44 either alone or with an antiseptic agent. The deodorizing agent may be introduced into container chamber 20 to minimize odors of the collected urine.

I claim:

1. A device for collecting urine from a patient, comprising:
    a container having a drainage tube and a chamber to receive urine, and a rigid header above the chamber; and
    receptacle means permanently secured to the container header and having a cavity, a liquid antiseptic agent in said cavity, with the cavity communicating with the container chamber directly through means defining an opening having a sufficiently small internal diameter so as to impede the passage of the agent therethrough under ordinary ambient pressure, and means for generating pressure above ambient pressure in the cavity to cause dispensing of said antiseptic agent from the cavity to the container chamber through said opening, to thereby minimize the possibility of contamination to the patient's bladder caused by retrograde bacteria movement from collected urine in the container through the drainage tube, said receptacle means and cavity being completely sealed from the ambient atmosphere when the antiseptic agent is being dispensed from the cavity into the container.

2. The device of claim 1 wherein said receptacle means has relatively rigid walls defining said cavity.

3. The device of claim 1 wherein the pressure-generating means comprises a flexible bellows attached to a wall of said receptacle means and communicating with said cavity.

4. The device of claim 1 including valve means communicating with said cavity to permit placement of said antiseptic agent in said cavity.

5. The device of claim 1 wherein the container has a pair of opposed flexible walls defining said chamber.

* * * * *